United States Patent [19]

Psaar et al.

[11] Patent Number: 4,931,567
[45] Date of Patent: Jun. 5, 1990

[54] BIS(INDOLYL)ETHYLENE COMPOUNDS

[75] Inventors: Hubertus Psaar; Horst Berneth, both of Leverkusen, Fed. Rep. of Germany

[73] Assignee: Bayer Aktiengesellschaft, Leverkusen, Fed. Rep. of Germany

[21] Appl. No.: 409,186

[22] Filed: Sep. 19, 1989

Related U.S. Application Data

[62] Division of Ser. No. 261,945, Oct. 24, 1988.

[30] Foreign Application Priority Data

Nov. 11, 1987 [DE] Fed. Rep. of Germany ....... 3738237

[51] Int. Cl.$^5$ ............................................. C07D 403/06
[52] U.S. Cl. ................................................. 548/455
[58] Field of Search ......................................... 548/455

[56] References Cited

FOREIGN PATENT DOCUMENTS 3738237  5/1989  Fed. Rep. of Germany ...... 548/455
1403617  5/1965  France ................................ 548/455

Primary Examiner—David B. Springer
Attorney, Agent, or Firm—Sprung Horn Kramer & Woods

[57] ABSTRACT

Bis(indolyl)ethylenes of the formula

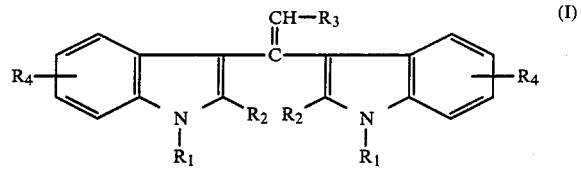

wherein
$R_1$ denotes hydrogen, alkyl, aralkyl or aryl,
$R_2$ denotes hydrogen, alkyl or aryl,
$R_3$ denotes hydrogen, alkyl, alkenyl, COOH or aryl and
$R_4$ denotes hydrogen, alkyl, alkoxy, cycloalkoxy or halogen, and these substituents, in turn, can carry non-ionic radicals or a carboxyl group, are obtained by reaction of indoles of the formula

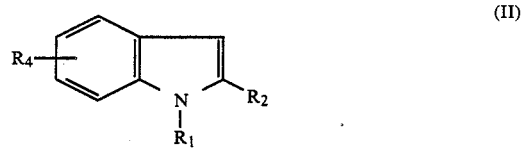

with carboxylic acids of the formula

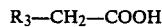

their chlorides, esters, for example alkyl esters, or anhydrides in the presence of phosphorus oxychloride.

3 Claims, No Drawings

BIS(INDOLYL)ETHYLENE COMPOUNDS

This is a division of application Ser. No. 07/261,945, filed 10/24/88, now pending.

The invention relates to a process for the preparation of bis(indolyl)ethylenes of the formula

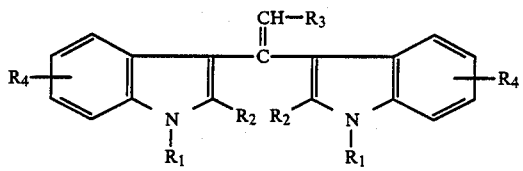

wherein
- $R_1$ denotes hydrogen, alkyl, aralkyl or aryl,
- $R_2$ denotes hydrogen, alkyl or aryl,
- $R_3$ denotes hydrogen, alkyl, alkenyl, COOH or aryl and
- $R_4$ denotes hydrogen, alkyl, alkoxy, cycloalkoxy or halogen, and these substituents, in turn, can carry non-ionic radicals or a carboxyl group, by reaction of indoles of the formula

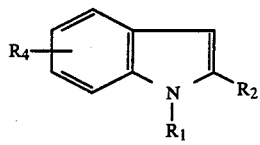

with carboxylic acids of the formula

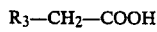

their chlorides, esters, for example alkyl esters, or anhydrides in the presence of phosphorus oxychloride.

Preferably, alkoxy stands for $C_1$-$C_{12}$-alkoxy, alkyl stands for $C_1$-$C_{12}$-alkyl, alkenyl stands for $C_2$$C_{12}$-alkenyl, aryl stands for phenyl, aralkyl stands for benzyl or phenethyl, cycloalkoxy stands for cyclohexoxy or cyclopentoxy and halogen stands for fluorine, chlorine or bromine, in particular chlorine.

Non-ionic radicals which should be mentioned are, for example, halogen, in particular chlorine, $C_1$-$C_4$-alkoxy, cyano and for the cyclic substituents, in addition $C_1$-$C_4$-alkyl.

The preferred reaction temperature is 50° C. to 105° C., and the preferred reaction time is between 20 minutes and 3 hours. The molar ratio of (II) : (III) should preferably be 2:1 at most.

Phosphorus oxychloride is advantageously employed in a molar ratio of 1.5 to 2:1 relative to (III) or its derivatives.

The reaction can be carried out with or without solvent, it being intended that the amount of phosphorus oxychloride is measured in the last case such that this simultaneously acts as the solvent. Aromatics, alkylated aromatics or chlorinated aromatics can be employed as the solvent. Suitable solvents are, for example, toluene, xylene, chlorobenzene or dichlorobenzene.

The process makes possible the preparation of the compounds (I) in a simple manner with high yield.

The invention further relates to bis(indolyl)ethylenes of the formula

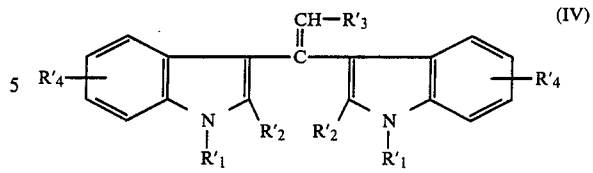

wherein either
(a) $R'_1$ denotes $C_2$-$C_{12}$-alkyl or benzyl, $R'_2$ and $R'_3$ denote hydrogen, alkyl or benzyl, $R'_4$ denotes hydrogen, alkyl, alkoxy or halogen, and phenyl and benzyl, each of which can be substituted by alkyl, alkoxy or halogen, or
(b) $R'_1$ denotes hydrogen, alkyl, or benzyl which can be substituted by alkyl, alkoxy or halogen, and $R'_4$ denotes alkyl, alkoxy or halogen, and $R'_2$ and $R'_3$ have the abovementioned meaning, or
(c) $R'_1$ denotes hydrogen, alkyl, or benzyl which can be substituted by alkyl, alkoxy or halogen, $R'_2$ denotes phenyl which can be substituted by alkyl, alkoxy or halogen, $R'_3$ denotes hydrogen, alkyl, or phenyl which can be substituted by alkyl, alkoxy or halogen, and $R'_4$ denotes hydrogen, alkyl, alkoxy or halogen, or
(d) $R'_1$ denotes hydrogen, alkyl, or benzyl which can be substituted by alkyl, alkoxy or halogen, $R'_2$ denotes phenyl, $R'_3$ denotes alkyl or phenyl and $R'_4$ denotes hydrogen, alkyl, alkoxy or halogen, and wherein alkyl—when not named separately—stands for $C_1$-$C_{12}$-alkyl and alkoxy stands for $C_1$-$C_{12}$-alkoxy and the alkyl radicals can be substituted by chlorine, cyano or carboxyl.

The compounds (c) and (d) are particularly preferred.

The compounds of the formula (I) are valuable intermediates for colour formers, which are described, for example, in DE-A-3,738,240.

EXAMPLE 1

20.7 parts by weight of 1-methyl-2-phenylindole are heated to 80° to 90° C. with stirring in 30 ml of phosphorus oxychloride. At this temperature, 5.3 parts by weight of acetic anhydride are added dropwise and the batch is stirred for 30 minutes at 100° C. The mixture is then discharged onto 200 parts by weight of ice water, rendered alkaline with 10 % strength sodium hydroxide solution, stirred for 15 hours at room temperature, and the precipitate is filtered off with suction and recrystallized from dimethylformamide.

Yield: 20.3 parts by weight; m.p.: 192°–194° C.

The compound has the formula:

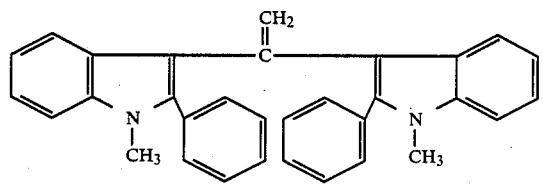

EXAMPLE 2

20.7 parts by weight of 1-methyl-2-phenylindole are heated to 90° C. in 50 ml of phosphorus oxychloride and 4.9 parts by weight of propionic acid are added dropwise at this temperature. After 30 minutes, the mixture is cooled to room temperature and 100 ml of methanol are slowly added. The batch is subsequentially stirred into a mixture of 500 ml of conc. ammonia and 500 ml of water. The product is filtered off with suction, stirred with methanol and dried at 50° C. in vacuo.

Yield: 22.1 parts by weight
m.p.: 184°–186° C.

The compound has the formula:

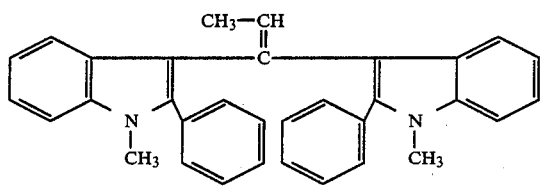

EXAMPLE 3

If 10 parts by weight of butyrolactone are added dropwise to the batch instead of propionic acid according to Example 2, then the bis(indolyl)ethylene of the formula

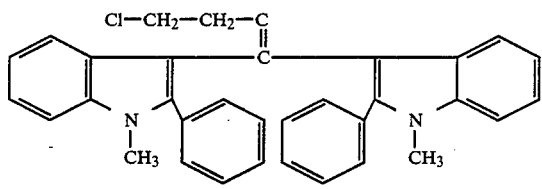

is obtained.

Yield: 24.5 parts by weight
m.p.: 101°–103° C.

The compounds of the formula

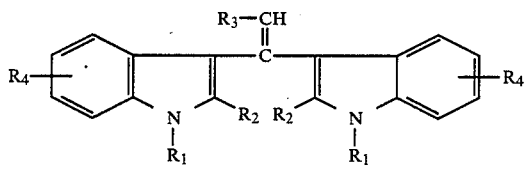

are prepared analogously to Example 1.

| Example | $R_1$ | $R_2$ | $R_3$ | $R_4$ | m.p. |
|---|---|---|---|---|---|
| 4 | $CH_3$ | $CH_3$ | H | H | 173° C. |
| 5 | $CH_3$ | H | H | H | 142–143° C. |
| 6 | $CH_3$ | $CH_3$ | $CH_3$ | H | 101–103° C. |
| 7 | $C_4H_9$ | $CH_3$ | H | H | |
| 8 | $CH_3$ | $CH_3$ | $C_{10}H_{21}$ | H | 97–99° C. |
| 9 | $CH_3$ | $C_6H_5$ | $CH_2$—COOH | H | 108–112° C. |
| 10 | $CH_3$ | $C_6H_5$ | $CH=CH_2$ | H | 165–167° C. |
| 11 | $C_2H_4CN$ | $C_6H_5$ | H | H | 210° C. |
| 12 | $C_2H_4COOH$ | $C_6H_5$ | H | H | 220° C. |
| 13 | $C_4H_9$ | $C_6H_5$ | H | H | 89–91° C. |
| 14 | $C_6H_5CH_2$ | $C_6H_5$ | H | H | 238–240° C. |
| 15 | $C_6H_5CH_2$ | $CH_3$ | H | H | 148–149° C. |
| 16 | $CH_3$ | $C_6H_4$, 4-$OCH_3$ | H | H | 172–174° C. |
| 17 | $CH_3$ | $C_6H_4$, 4-Cl | H | H | 210° C. |
| 18 | $CH_3$ | $C_6H_5$ | H | 6-Cl | 214–217° C. |
| 19 | $CH_3$ | $C_6H_5$ | H | 5-$CH_3$ | 225–227° C. |
| 20 | $C_2H_5$ | $C_6H_5$ | H | H | 160° C. |
| 21 | $CH_3$ | $C_6H_5$ | Cl | H | 182,5° C. |
| 22 | H | $C_6H_5$ | H | H | 244–246° C. |
| 23 | H | $C_6H_5$ | $CH_3$ | H | 169° C. |
| 24 | $C_6H_5CH_2$ | $C_6H_5$ | $CH_3$ | H | 80° C. |

We claim:
1. Bis(indolyl)ethylenes of the formula

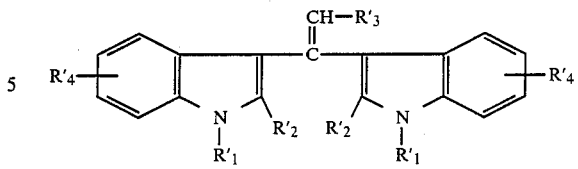

wherein either
(a) $R'_1$ denotes $C_2$–$C_{12}$-alkyl or benzyl, $R'_2$ and $R'_3$ denote hydrogen, alkyl or benzyl, $R'_4$ denotes hydrogen, alkyl, alkoxy or halogen, and phenyl and benzyl, each of which can be substituted by alkyl, alkoxy or halogen, or
(b) $R'_1$ denotes hydrogen, alkyl, or benzyl which can be substituted by alkyl, alkoxy or halogen, and $R'_4$ denotes alkyl, alkoxy or halogen, and $R'_2$ and $R'_3$ have the abovementioned meaning, or
(c) $R'_1$ denotes hydrogen, alkyl, or benzyl whch can be substituted by alkyl, alkoxy or halogen, $R'_2$ denotes phenyl which can be substituted by alkyl, alkoxy or halogen, $R'_3$ denotes hydrogen, alkyl, or phenyl which can be substituted by alkyl, alkoxy or halogen, and $R'_4$ denotes hydrogen, alkyl, alkoxy or halogen, or
(d) $R'_1$ denotes hydrogen, alkyl, or benzyl which can be substituted by alkyl, alkoxy or halogen, $R'_2$ denotes phenyl, $R'_3$ denotes alkyl or phenyl and $R'_4$ denotes hydrogen, alkyl, alkoxy or halogen, and wherein alkyl—when not named separately—stands for $C_1$–$C_{12}$-alkyl and alkoxy stands for $C_1$–$C_{12}$-alkoxy and the alkyl radicals can be substituted by chlorine, cyano or carboxyl.

2. Bis(indolyl)ethylenes according to claim 1, characterized in that
$R'_1$ denotes hydrogen, alkyl or benzyl,
$R'_2$ denotes phenyl which is substituted by alkyl, alkoxy or halogen,
$R'_3$ denotes hydrogen, alkyl or phenyl, and
$R'_4$ denotes hydrogen, alkyl, alkoxy or halogen, and the alkyl and alkoxy radicals have 1 to 12 C atoms.

3. Bis(indolyl)ethylenes according to claim 1, characterized in that
$R'_1$ denotes hydrogen, alkyl or benzyl,
$R'_2$ denotes phenyl,
$R'_3$ denotes alkyl or phenyl and
$R'_4$ denotes hydrogen, alkyl, alkoxy or halogen, and the alkyl and alkoxy radicals have 1–12 C atoms.

* * * * *